US012376998B2

(12) United States Patent
Strong et al.

(10) Patent No.: US 12,376,998 B2
(45) Date of Patent: *Aug. 5, 2025

(54) METHOD AND APPARATUS FOR MAKING TAMPONS

(71) Applicant: The Procter & Gamble Company, Cincinnati, OH (US)

(72) Inventors: Kevin Charles Strong, Loveland, OH (US); Evan Joseph Durling, West Chester, OH (US); Hinrich Knuth, Mason, OH (US); Khalid Qureshi, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/748,285

(22) Filed: Jun. 20, 2024

(65) Prior Publication Data
US 2024/0335335 A1 Oct. 10, 2024

Related U.S. Application Data

(63) Continuation of application No. 18/459,475, filed on Sep. 1, 2023, now Pat. No. 12,042,363, which is a
(Continued)

(51) Int. Cl.
*A61F 13/20* (2006.01)
*B65H 20/00* (2006.01)
(Continued)

(52) U.S. Cl.
CPC ...... *A61F 13/2085* (2013.01); *A61F 13/2082* (2013.01); *B65H 20/00* (2013.01); *B65H 35/00* (2013.01); *D05B 3/12* (2013.01)

(58) Field of Classification Search
CPC .......... A61F 13/15739; A61F 13/15764; A61F 13/2085; A61F 13/2082
See application file for complete search history.

(56) References Cited

U.S. PATENT DOCUMENTS

| 1,932,383 A | 10/1933 | Richardson |
| 2,123,750 A | 7/1938 | Schulz |

(Continued)

FOREIGN PATENT DOCUMENTS

| CN | 1283979 A | 2/2001 |
| CN | 1516569 A | 7/2004 |

(Continued)

OTHER PUBLICATIONS

PCT Search Report and Written Opinion for PCT/US2019/064120 dated Mar. 12, 2020, 13 pages.
(Continued)

*Primary Examiner* — Barbara J Musser
(74) *Attorney, Agent, or Firm* — Sarah M. DeCristofaro

(57) ABSTRACT

The present disclosure relates to apparatuses and methods for making tampons including primary and secondary absorbent members. During assembly, primary absorbent members, a continuous length of secondary absorbent members, and a continuous cord are advanced in a machine direction. Leading edges of the primary absorbent members are separated from each other in the machine direction by a pitch distance. Discrete secondary absorbent members are cut from the continuous length of secondary absorbent members. Leading edges of the discrete secondary absorbent members are also separated from each other in the machine direction by the pitch distance. The continuous cord is positioned on the secondary absorbent members. And a secondary absorbent member is positioned in contact with a primary absorbent member. A thread is combined with the (Continued)

continuous cord, the secondary absorbent member, and the primary absorbent member.

19 Claims, 11 Drawing Sheets

Related U.S. Application Data continuation of application No. 16/716,550, filed on Dec. 17, 2019, now Pat. No. 11,779,494.

(60) Provisional application No. 62/780,388, filed on Dec. 17, 2018.

(51) Int. Cl.
  B65H 35/00 (2006.01)
  D05B 3/12 (2006.01)

(56) References Cited

U.S. PATENT DOCUMENTS

| | | | |
|---|---|---|---|
| 2,391,343 | A | 12/1945 | Otto |
| 2,412,391 | A | 12/1946 | Crockford |
| 2,412,861 | A | 12/1946 | William |
| 2,499,414 | A | 3/1950 | Rabell |
| 3,397,695 | A | 8/1968 | Voss |
| 3,731,687 | A | 5/1973 | Glassman |
| 3,732,866 | A | 5/1973 | Accavallo |
| RE27,677 | E | 6/1973 | Glassman |
| 3,811,445 | A | 5/1974 | Dostal |
| 4,200,101 | A | 4/1980 | Glassman |
| 4,318,407 | A | 3/1982 | Woon |
| 4,335,720 | A | 6/1982 | Glassman |
| 4,624,668 | A | 11/1986 | Siegers |
| 4,835,042 | A | 5/1989 | Dohzono |
| 5,891,123 | A | 4/1999 | Balzar |
| 6,186,995 | B1 | 2/2001 | Tharpe, Jr. |
| 6,258,074 | B1 | 7/2001 | Prazak |
| 6,258,075 | B1 | 7/2001 | Taylor |
| 6,840,927 | B2 | 1/2005 | Hasse |
| 7,799,966 | B2 | 9/2010 | Williams |
| 8,827,974 | B2 | 9/2014 | Schmidt-forst |
| 9,237,970 | B2 * | 1/2016 | Iida ............... B65H 35/00 |
| 11,779,494 | B2 | 10/2023 | Strong |
| 11,925,535 | B2 | 3/2024 | Strong |
| 12,042,363 | B2 | 7/2024 | Strong |
| 2001/0021839 | A1 | 9/2001 | Kashiwagi |
| 2003/0097106 | A1 | 5/2003 | Hasse et al. |
| 2003/0097108 | A1 | 5/2003 | Hasse et al. |
| 2003/0097112 | A1 | 5/2003 | Gilbert et al. |
| 2004/0000193 | A1 | 1/2004 | Grotendorst |
| 2004/0019317 | A1 | 1/2004 | Takagi |
| 2005/0055003 | A1 | 3/2005 | Bittner et al. |
| 2005/0096619 | A1 | 5/2005 | Costa |
| 2006/0025742 | A1 | 2/2006 | Hasse et al. |
| 2007/0016156 | A1 | 1/2007 | Burgdorf et al. |
| 2007/0260211 | A1 | 11/2007 | Schmidt-forst |
| 2008/0132868 | A1 | 6/2008 | Jorgensen |
| 2008/0262463 | A1 | 10/2008 | Noel et al. |
| 2008/0275411 | A1 | 11/2008 | Hughes et al. |
| 2009/0260205 | A1 | 10/2009 | Binner et al. |
| 2010/0069866 | A1 | 3/2010 | Binner et al. |
| 2010/0130953 | A1 | 5/2010 | Fung et al. |
| 2010/0174262 | A1 | 7/2010 | Watanabe |
| 2010/0268182 | A1 | 10/2010 | Edgett |
| 2012/0053550 | A1 | 3/2012 | Kinoshita et al. |
| 2012/0101462 | A1 | 4/2012 | Lee |
| 2012/0277704 | A1 | 11/2012 | Marinelli |
| 2013/0138071 | A1 | 5/2013 | Fung et al. |
| 2013/0160259 | A1 | 6/2013 | Mcdaniel et al. |
| 2015/0157511 | A1 | 6/2015 | Strong |
| 2015/0374558 | A1 | 12/2015 | Strong et al. |
| 2018/0125724 | A1 | 5/2018 | Brown et al. |
| 2020/0188190 | A1 | 6/2020 | Strong |
| 2024/0164952 | A1 | 5/2024 | Strong |
| 2024/0207104 | A1 | 6/2024 | Strong |

FOREIGN PATENT DOCUMENTS

| | | |
|---|---|---|
| CN | 101874756 A | 11/2010 |
| WO | 0061052 A1 | 10/2000 |
| WO | 2000061052 A1 | 10/2000 |
| WO | 02058609 A2 | 8/2002 |
| WO | 02058614 A1 | 8/2002 |
| WO | 03022196 A2 | 3/2003 |
| WO | 2005063161 A1 | 7/2005 |
| WO | 2005112861 A1 | 12/2005 |
| WO | 2007078413 A1 | 7/2007 |
| WO | 2016207242 A1 | 12/2016 |

OTHER PUBLICATIONS

All Office Actions; U.S. Appl. No. 16/716,556, filed Dec. 17, 2019.
All Office Actions; U.S. Appl. No. 16/716,553, filed Dec. 17, 2019.
All Office Actions; U.S. Appl. No. 16/716,550, filed Dec. 17, 2019.
All Office Actions; U.S. Appl. No. 18/429,861, filed Feb. 1, 2024.
All Office Actions; U.S. Appl. No. 18/459,475, filed Sep. 1, 2023.
All Office Actions; U.S. Appl. No. 18/599,355, filed Mar. 8, 2024.
Fiery Software. Delta E, Delta H, Delta T: What Does It Mean?. Online retrieved from chrome extension://efaidnbmnn-nibpcajpcglclefindmkaj/https://help.fiery.com/fieryxf/KnowledgeBase/ColorManagement/Delta%20E_H_T.pdf, dated 2023, pp. 04.
Gopalakrishnan, "D. Spunbonded Nonwovens"—An Overview, Online retrieved from https://www.fibre2fashion.com/industry-article/1575/spunbonded-nonwovens-an-overview. Year: 2007, pp. 05.
McLoughlin, J, and Mitchell, A.; "Textiles and Fashion, Materials design and technology",Publishing, Retrieved from the Internet: URL:https://www.sciencedirect.com/science/article/pii/B9781845699314000167, Chapter 16, ISBN-978: 0-85709-561-9, Year 2015, pp. 379-411.

* cited by examiner

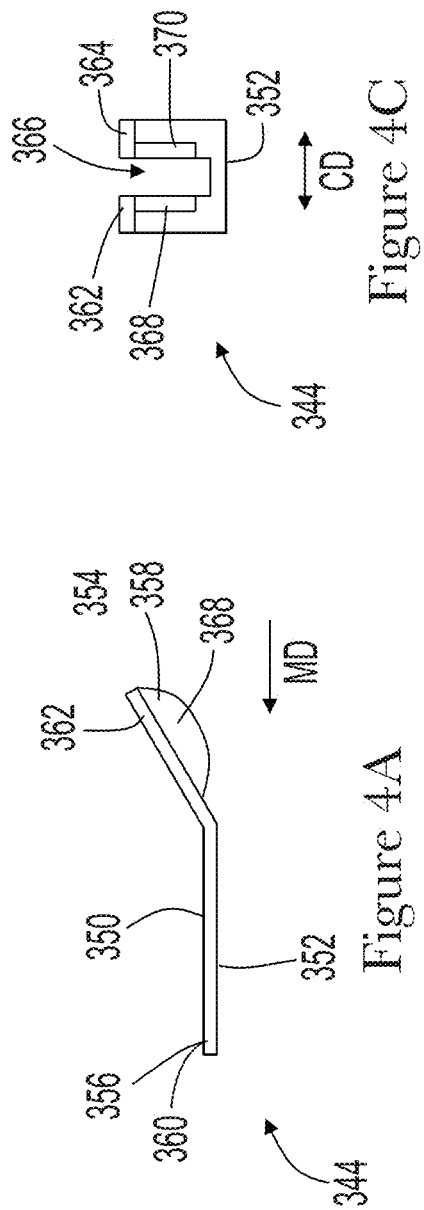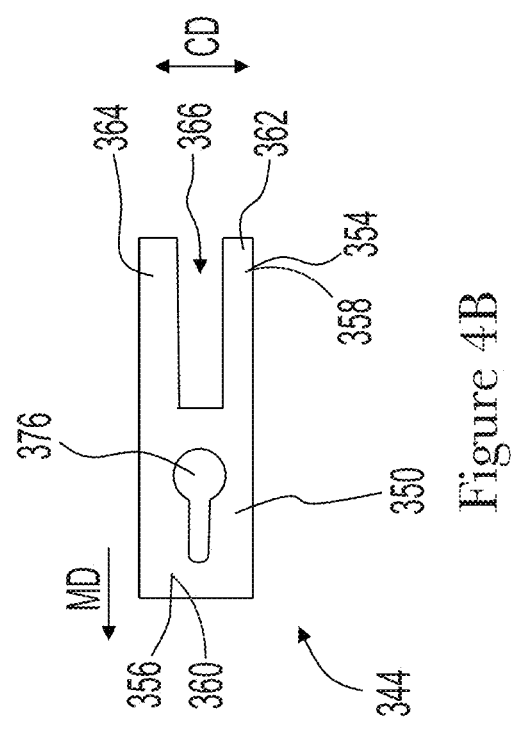

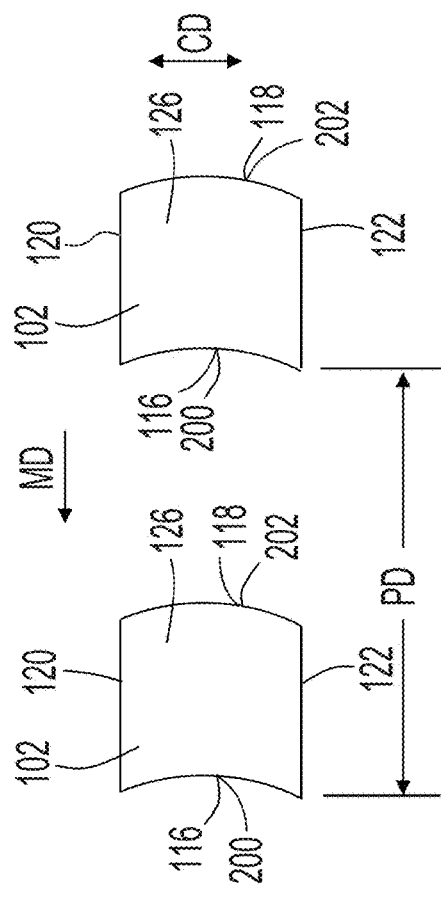
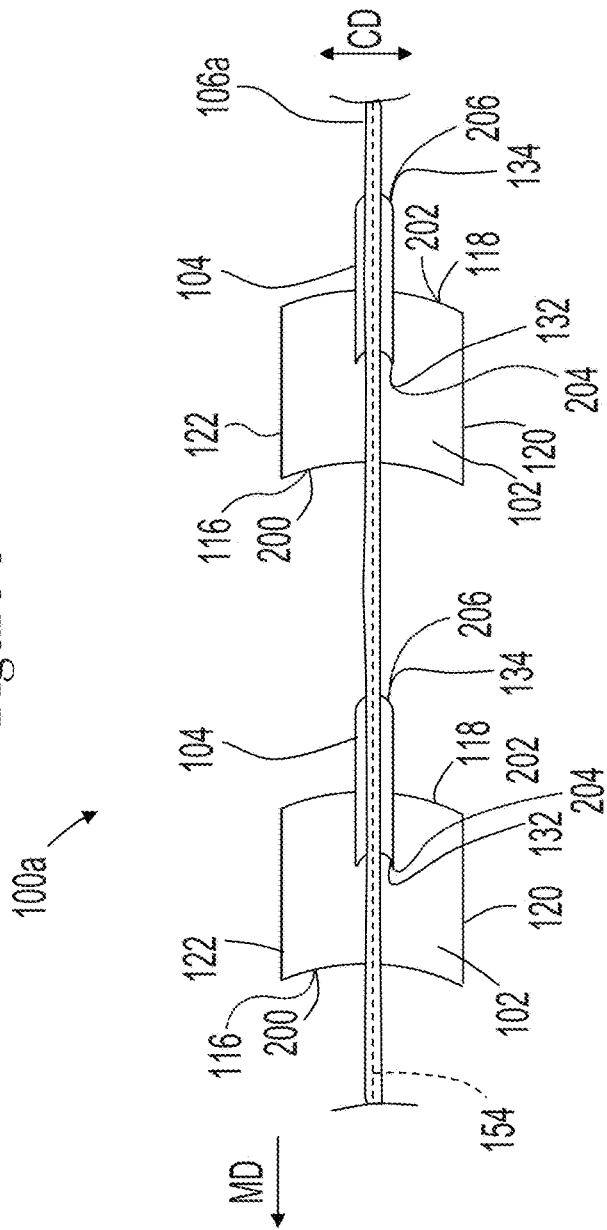

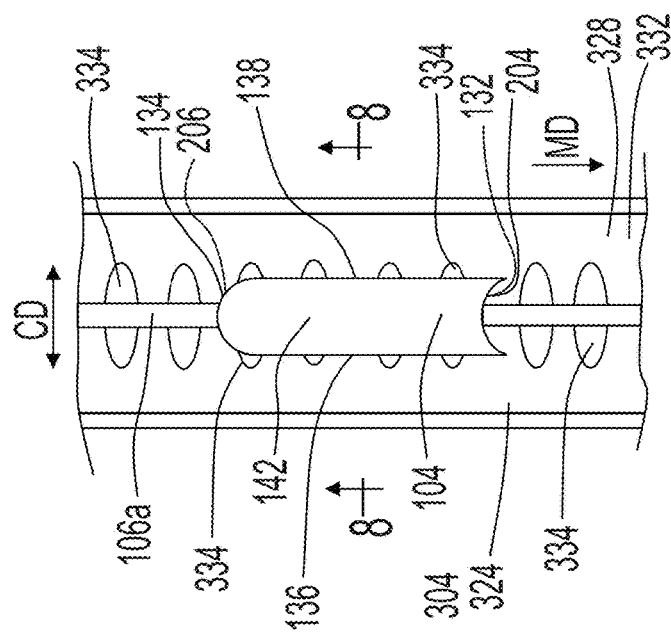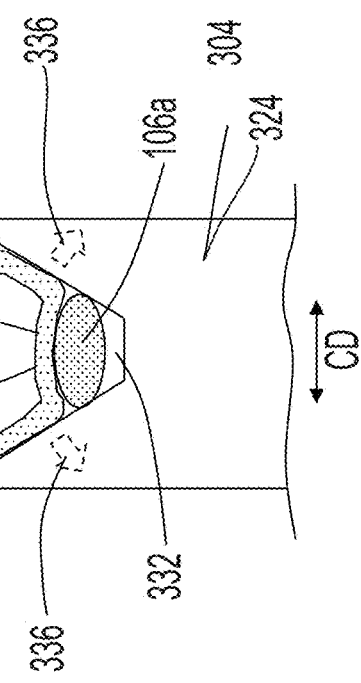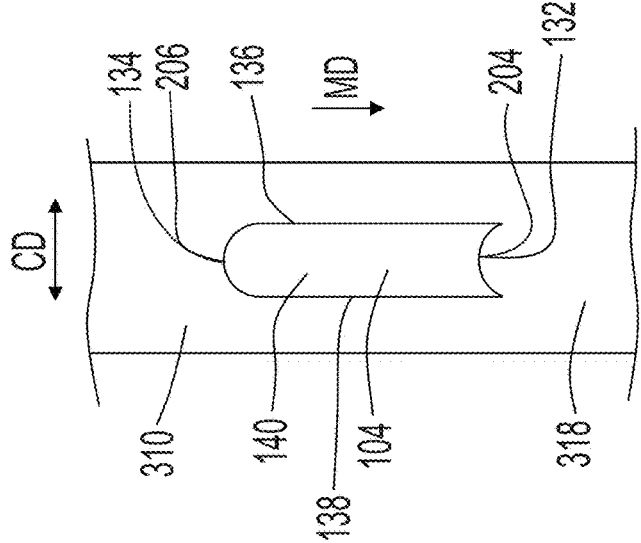

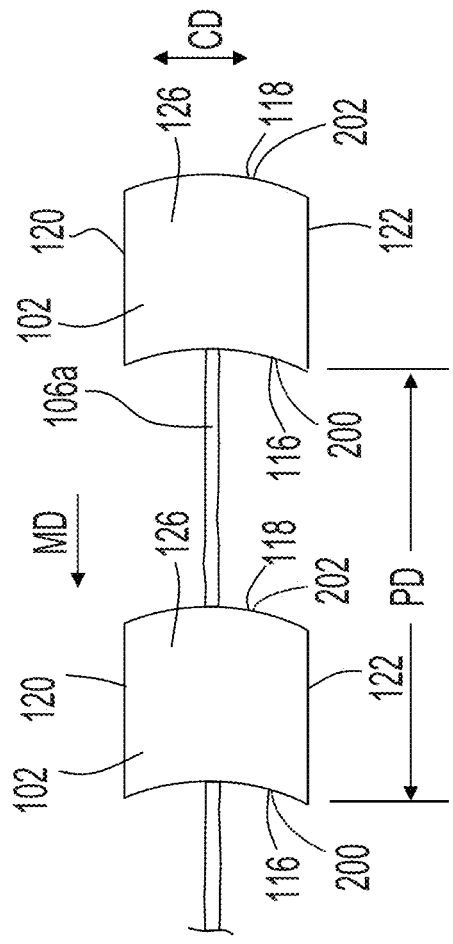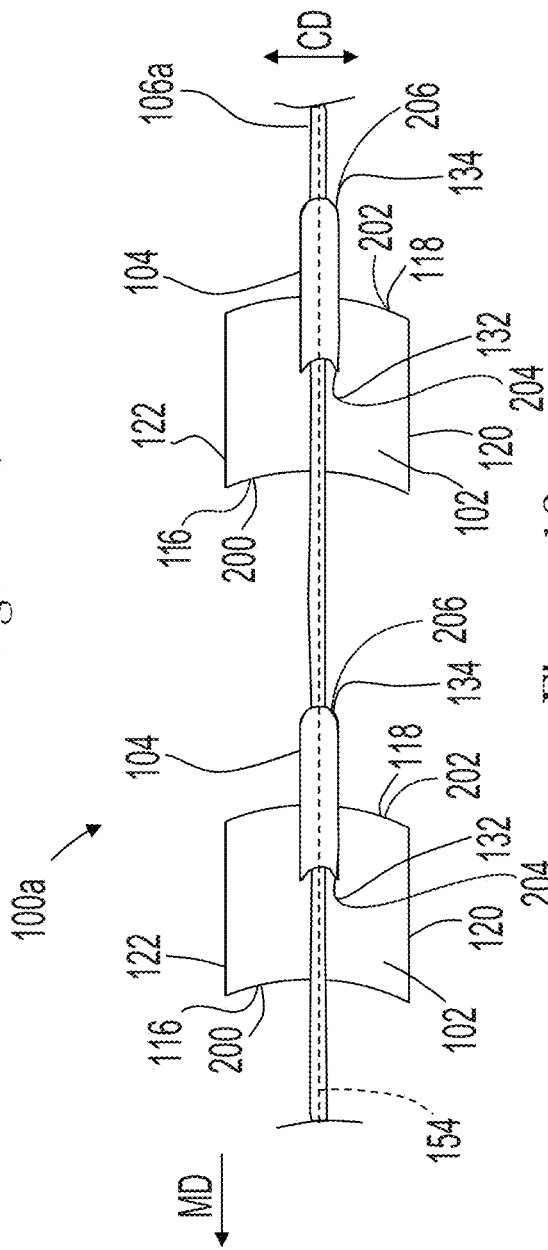

METHOD AND APPARATUS FOR MAKING TAMPONS

CROSS REFERENCE TO RELATED APPLICATION

This application is a continuation of, and claims priority under 35 U.S.C. § 120 to, U.S. patent application Ser. No. 18/459,475 filed on Sep. 1, 2023, which is a continuation of U.S. patent application Ser. No. 16/716,550 filed on Dec. 17, 2019, now U.S. Pat. No. 11,779,494, granted on Oct. 10, 2023, which claims the benefit, under 35 U.S.C. § 119 (e), of U.S. Provisional Patent Application Ser. No. 62/780,388 filed on Dec. 17, 2018, the entire disclosures of all of which are fully incorporated by reference herein.

FIELD OF THE INVENTION

The present disclosure relates to methods for manufacturing tampons, and more particularly, to apparatuses and methods for making tampons that include primary absorbent members and secondary absorbent members.

BACKGROUND OF THE INVENTION

A wide variety of absorbent catamenial tampons have been known in the art. Some currently commercially available tampons are made from absorbent material configured as an absorbent member which has been compressed into a substantially cylindrical form. Prior to compression, the absorbent member may be rolled, spirally wound, folded, or assembled as a rectangular pad of absorbent material. Conventional catamenial tampons may also be provided with a withdrawal cord connected with the absorbent member. During use, the withdrawal cord may extend out of a user's body following tampon insertion to allow for retrieval and disposal of the used tampon.

In order to provide the desired total absorbency, absorbent members may be formed from batts larger in size than a vaginal orifice. The batts are then compressed to a size with a corresponding increase in rigidity in order to facilitate insertion. As fluid is absorbed, these compressed tampons are configured to re-expand toward an original pre-compressed size, and to eventually become large enough to effectively cover the vaginal cavity and prevent fluid leakage. However, some compressed tampons may not always re-expand sufficiently, or fast enough, to provide a desired coverage against leakage. As such, suppliers of tampons have recognized various mechanisms by which tampons might fail to deliver superior performance. One such mechanism is often referred to in the art as "bypass" failure. Bypass failure occurs when menses travels along the length of the vagina without contacting the tampon, wherein the tampon fails to intercept the flowing menses.

In the past, different approaches have been attempted to address bypass and other forms of tampon failure. For example, some tampons may be constructed with a secondary absorbent material in addition to a compressed primary absorbent material. Advantages of such a secondary absorbent material may include an ability of the tampon to absorb bypass flow in the early stages of wear, as well as an ability of the tampon to absorb residual fluid which may have been "squeezed out" of a prior tampon during removal.

In some configurations, the secondary absorbent material may be made from material such as, for example, fibrous materials formed by a carding process. Various methods and apparatuses may be used to integrate such fibrous secondary absorbent material into assembled tampons. Some manufacturers have utilized the assembly process of withdrawal cords, such as mentioned above, to integrate the secondary absorbent material into the tampon assembly process. For example, in some operations, withdrawal cords may be constructed by advancing one or more strings through a tubular weaver. In turn, manufacturers of tampons with secondary absorbent material have utilized the tubular weaving process to incorporate the secondary absorbent material into the withdrawal cord construction. For example, fleeces of secondary absorbent material may be intermittently combined with the advancing string upstream of the weaver. As such, the string and intermittent lengths of secondary absorbent material advance through the weaver to create a continuous composite yarn wherein the withdrawal cord material and secondary absorbent material are interwoven. Discrete lengths of secondary absorbent material are intermittently formed on the continuous composite yarn. The continuous composite yarn may then be attached to the primary absorbent material during the assembly process with the discrete length of secondary absorbent material connected with the primary absorbent member in a desired location.

However, the above described tampon assembly operations may present various challenges and/or limitations. For example, some tampon manufacturing lines may operate at relatively high speeds. In contrast, the weaving process discussed above may be a relatively slow process with a relatively low throughput. As such, relatively numerous weaving operations may be required to produce sufficient quantities of composite yarn required by the relatively high speed tampon assembly processes. Requiring numerous weaving operations can result in higher costs and complexities for tampon manufacturers. In addition, composite yarn assembly may necessitate intertwining two materials with different properties. For example, in some tampon configurations, the string used to construct the withdrawal cord may be hydrophobic whereas the secondary absorbent material may be hydrophilic. As such, the composite yarn may be assembled such that some portions are constructed with hydrophilic and hydrophobic materials woven together. Such interwoven hydrophilic and hydrophobic materials function in divergent fashions, which in turn, may have a negative effect on the overall performance of the tampon. Further, some withdrawal cords made with a woven construction may be relatively more prone to frayed ends as compared to withdrawal cords constructed differently. Utilizing the above composite yarn assembly process limits the withdrawal cord and/or secondary absorbent material to a woven construction in circumstances wherein it may be preferable to construct the withdrawal cord and/or secondary absorbent material in different ways.

Consequently, it would be beneficial to provide methods and apparatuses for producing catamenial tampons with secondary absorbent materials and withdrawal cord constructions that can be provided so as to be assembled at relatively high speeds while eliminating or reducing the needed quantities of weaving operations and further providing manufactures with additional flexibilities with respect to material choices and/or construction.

SUMMARY OF THE INVENTION

In one form, a method for making a tampon comprises steps of: advancing primary absorbent members in a machine direction, wherein each primary absorbent member comprises a first surface and an opposing second surface extending in the machine direction between a leading edge and a trailing edge, wherein the leading edges of advancing the primary absorbent members are separated from each other in the machine direction by a pitch distance; advancing discrete secondary absorbent members, wherein each discrete secondary absorbent member extends in the machine direction between a leading edge and a trailing edge; separating the leading edges of the advancing discrete secondary absorbent members from each other in the machine direction by the pitch distance; advancing a continuous cord in the machine direction; positioning the continuous cord on a first discrete secondary absorbent member; positioning the first discrete secondary absorbent member in contact with a first primary absorbent member; combining the continuous cord, the first discrete secondary absorbent member, and the first primary absorbent member.

In another form, a method for making a tampon comprises steps of: advancing primary absorbent members at a first speed, S1, wherein each primary absorbent member comprises a first surface and an opposing second surface extending in the machine direction between a leading edge and a trailing edge, wherein the leading edges of advancing the primary absorbent members are separated from each other in the machine direction by a pitch distance; advancing a continuous length of secondary absorbent members at a second speed, S2, wherein the second speed, S2, is less than the first speed, S1; cutting discrete secondary absorbent members from the continuous length of secondary absorbent members, wherein each discrete secondary absorbent member extends in the machine direction between a leading edge and a trailing edge; accelerating the discrete secondary absorbent members from the second speed, S2, to the first speed, S1; advancing a continuous cord in the machine direction; positioning the continuous cord on the discrete secondary absorbent members; positioning the first discrete secondary absorbent member in contact with a first primary absorbent member; and combining the continuous cord, the first discrete secondary absorbent member, and the first primary absorbent member.

In yet another form, an apparatus for making tampons comprises: an anvil roll adapted to rotate about a first axis of rotation; a knife roll adapted to rotate about a second axis of rotation, the knife roll positioned adjacent the anvil roll to define a first nip between the knife roll and the anvil roll; a transfer wheel adapted to rotate about a third axis of rotation, the transfer wheel positioned adjacent the anvil roll or the knife roll to define a second nip between the transfer wheel and the knife roll or the anvil roll; a presser foot comprising a first end portion and a second end portion, wherein the first end portion comprises a first projection and a second projection separated in by a notch, and wherein a portion of the transfer wheel is positioned in the notch.

In still another form, a catamenial tampon for use within the vaginal space of a female wearer comprises: a primary absorbent member comprising a first surface and an opposing second surface extending between a first end edge and a second end edge; a secondary absorbent member extends between a first end edge and a second end edge, wherein the second surface of the secondary absorbent member is positioned in contact with and in a facing relationship with the first surface of the primary absorbent member; a cord on the positioned on the first surface of the secondary absorbent member; and at least two threads, wherein the cord, the secondary absorbent member, and the primary absorbent member are sewn together with the at least two threads.

In still another form, a method for making a tampon comprises steps of: advancing primary absorbent members in a machine direction, wherein each primary absorbent member comprises a first surface and an opposing second surface extending in the machine direction between a leading edge and a trailing edge, wherein the leading edges of advancing the primary absorbent members are separated from each other in the machine direction by a pitch distance; advancing discrete secondary absorbent members, wherein each discrete secondary absorbent member extends in the machine direction between a leading edge and a trailing edge; separating the leading edges of the advancing discrete secondary absorbent members from each other in the machine direction by the pitch distance; advancing a continuous cord in the machine direction; positioning the continuous cord on a first primary absorbent member; positioning a first discrete secondary absorbent member in contact with the first primary absorbent member; and combining the continuous cord, the first discrete secondary absorbent member, and the first primary absorbent member.

BRIEF DESCRIPTION OF THE DRAWINGS

FIG. 4A is a detailed right side view of a presser foot.

FIG. 4B is a top side view of the presser foot of FIG. 4A.

FIG. 4C is a front side view of the presser foot of FIG. 4A.

FIG. 5 is a sectional view of the apparatus from FIG. 4 taken along line 5-5 showing advancing primary absorbent members.

FIG. 6 is a sectional view of the apparatus from FIG. 4 taken along line 6-6 showing a secondary absorbent member advancing on a knife roll.

FIG. 7 is a cross-sectional view of the apparatus from FIG. 4 taken along line 7-7 showing a secondary absorbent member advancing on a transfer wheel.

FIG. 8 is a sectional view of the apparatus from FIG. 7 taken along line 8-8 showing the secondary absorbent member and withdrawal cord on the transfer wheel.

FIG. 9 is a sectional view of the apparatus from FIG. 4 taken along line 9-9 showing a continuous length of tampons.

FIG. 12 is a sectional view of the apparatus from FIG. 11 taken along line 12-12 showing advancing primary absorbent members and a continuous withdrawal cord.

FIG. 13 is a sectional view of the apparatus from FIG. 11 taken along line 13-13 showing a continuous length of tampons.

DETAILED DESCRIPTION OF THE INVENTION

Figure 1:
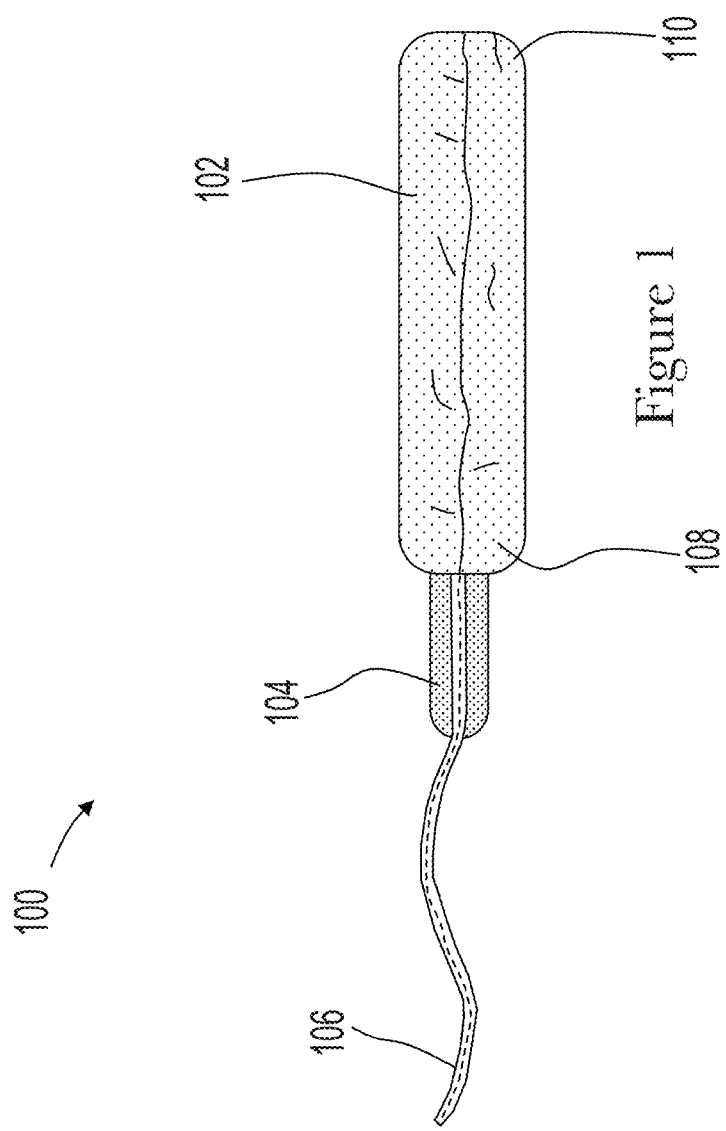
FIG. 1 is a front view of an example catamenial tampon.

The following term explanations may be useful in understanding the present disclosure:

As used herein the term "tampon" refers to any type of absorbent structure which is inserted into the vaginal canal or other body cavities for the absorption of fluid therefrom. Tampons are constructed from an absorbent material that may be compressed into a generally cylindrical configuration in the radial direction, axially along the longitudinal axis or in both the radial and axial directions to provide a tampon which is of a size and stability to allow insertion within the vagina or other body cavity. A tampon which has been so compressed is referred to herein as a "self-sustaining" form. That is, the degree of compression applied to the absorbent material of the tampon pledget is sufficient so that in the subsequent absence of the external forces, the resulting tampon will tend to retain its general shape and size. Tampons have an insertion end, withdrawal end, a length, a width, a longitudinal axis and a radial axis. The tampon's length can be measured from the insertion end to the withdrawal end along the longitudinal axis. In some examples, a compressed tampon for human use may have length within a range from about 30 mm to about 60 mm. A tampon may be straight or non-linear in shape, such as curved along the longitudinal axis. In some examples, a compressed tampon is within a range from about 8 mm to about 20 mm wide. The width of a tampon, unless otherwise stated in the specification, corresponds to the distance across the largest cross-section, along the length of the tampon and perpendicular to the longitudinal axis of the tampon.

The term "stabilized," as used herein, refers to a tampon in a self-sustaining state wherein it has overcome the natural tendency to re-expand to the original size, shape and volume of the absorbent material and overwrap, which comprise the pledget.

As used herein the terms "pledget" or "tampon pledget" are intended to be interchangeable and refer to a construction of absorbent material prior to the compression of such construction into a tampon as described above. Tampon pledgets are sometimes referred to as a tampon blank, or a softwind, and the term "pledget" is intended to include such terms as well.

As used herein the terms "vaginal cavity," "within the vagina" and "vaginal interior," are intended to be synonymous and refer to the internal genitalia of the human female in the pudendal region of the body. The term "vaginal cavity" as used herein is intended to refer to the space located between the introitus of the vagina (sometimes referred to as the sphincter of the vagina) and the cervix and is not intended to include the interlabial space, including the floor of vestibule. The externally visible genitalia generally is not included within the term "vaginal cavity" as used herein.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

The term "nonwoven" refers herein to a material made from continuous (long) filaments (fibers) and/or discontinuous (short) filaments (fibers) by processes such as spunbonding, meltblowing, carding, and the like. Nonwovens do not have a woven or knitted filament pattern.

The term "machine direction" (MD) is used herein to refer to the direction of material flow through a process. In addition, relative placement and movement of material can be described as flowing in the machine direction through a process from upstream in the process to downstream in the process.

The term "cross direction" (CD) is used herein to refer to a direction that is generally perpendicular to the machine direction.

Aspects of the present disclosure relate to methods for manufacturing tampons, and more particularly, to apparatuses and methods for making tampons including primary absorbent members and secondary absorbent members. During the assembly process, primary absorbent members, a continuous length of secondary absorbent members, and a continuous cord may be advanced in a machine direction. Each primary absorbent member comprises a first surface and an opposing second surface extending in the machine direction between a leading edge and a trailing edge. The leading edges of advancing the primary absorbent members are separated from each other in the machine direction by a pitch distance. Discrete secondary absorbent members are cut from the continuous length of secondary absorbent members, wherein each discrete secondary absorbent member comprises a first surface and an opposing second surface extending in the machine direction between a leading edge and a trailing edge. The leading edges of the advancing discrete secondary absorbent members are also separated from each other in the machine direction by the pitch distance. As discussed in more detail below, the continuous cord is positioned on the first surface of the discrete secondary absorbent members. And the second surface of a discrete secondary absorbent member is positioned in contact with and in a facing relationship with the first surface of a primary absorbent member. Next, a thread is sewn through the continuous cord, the discrete secondary absorbent member, and the primary absorbent member. As such, the processes and apparatuses herein provide for the assembly of tampons having secondary absorbent members and withdrawal cords while at the same time eliminating the necessity to utilize a continuous composite yarn including an interwoven withdrawal cord material and secondary absorbent material.

Figure 2:
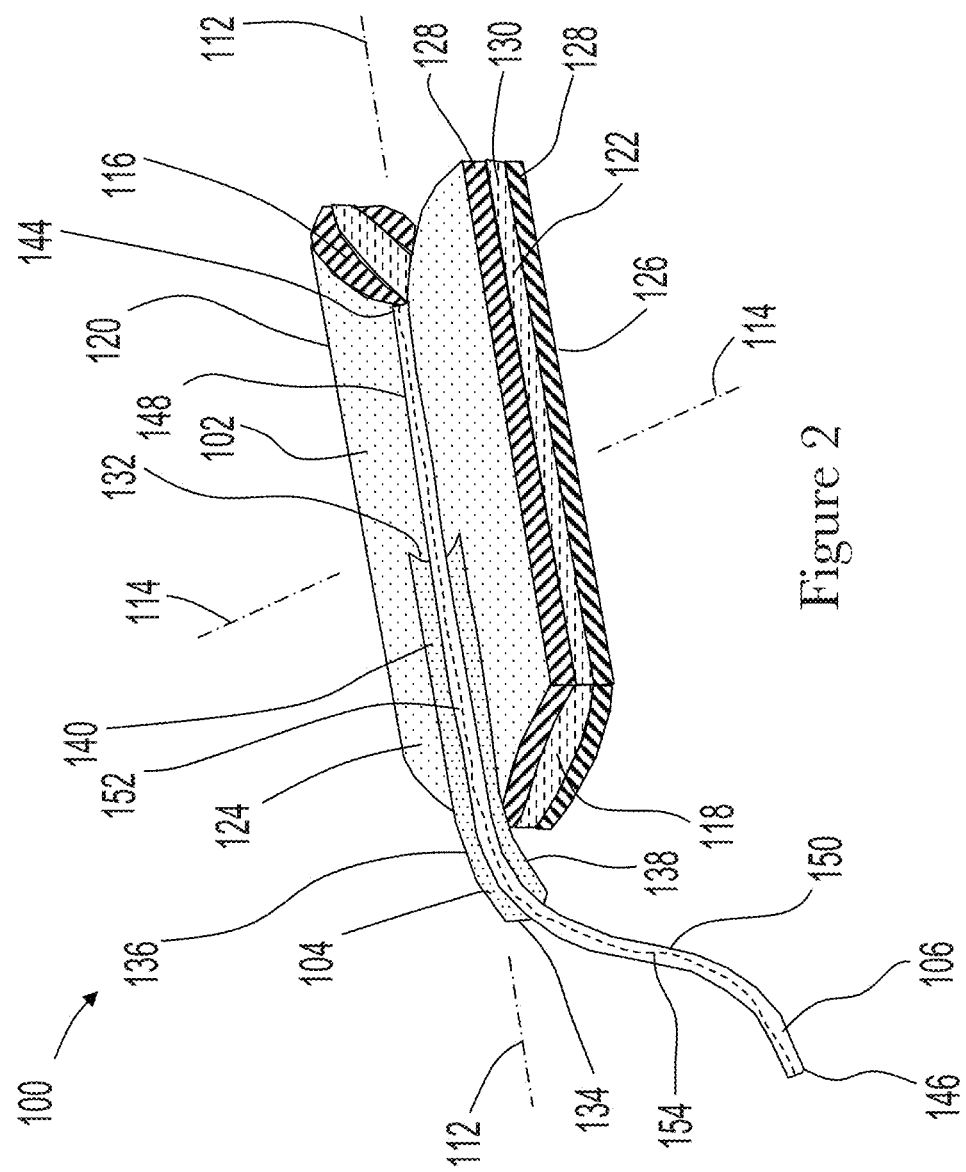
FIG. 2 is a perspective view of a tampon blank prior to compression into the tampon shown in FIG. 1.

It is to be appreciated that the systems and methods disclosed herein are applicable to work with various types of converting processes and/or machines adapted to manufacture tampons. For the purposes of a specific illustration, FIGS. 1 and 2 show an example of a tampon 100 that may be assembled in accordance with the methods and apparatuses disclosed herein. The primary absorbent member 102 can be compressed into a generally cylindrical configuration in the radial direction, the axial direction, or in both the radial and axial directions. While the primary absorbent member 102 may be compressed into a substantially cylindrical configuration as shown for example in FIG. 1, other shapes are also possible. Such shapes may include shapes having a cross section that may be described as oval, rectangular, triangular, trapezoidal, semi-circular, hourglass, serpentine, or other suitable shapes.

Figure 3:
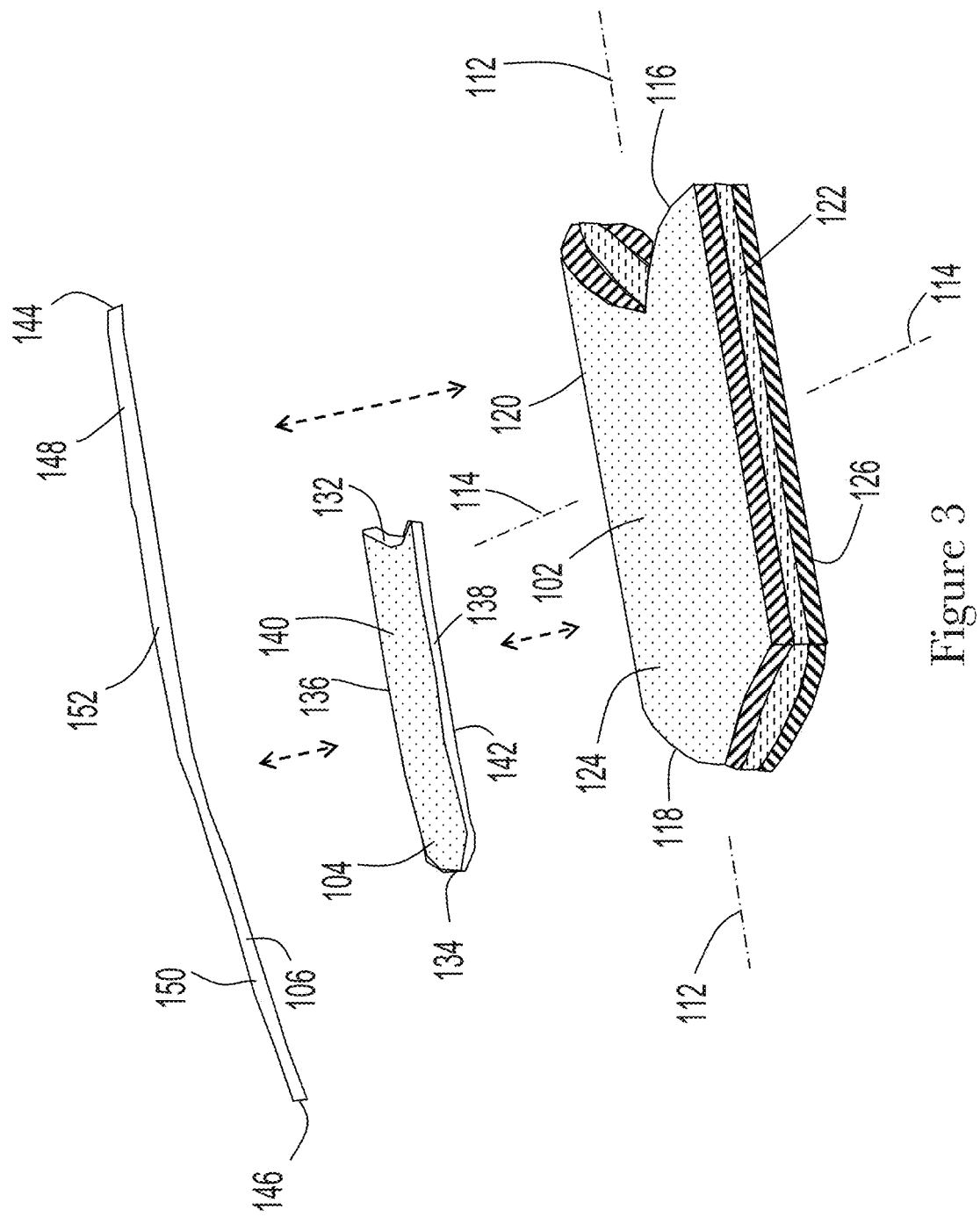
FIG. 3 is an exploded view of the tampon from FIG. 2.

As shown in FIGS. 1 and 2, the tampon 100 may include a primary absorbent member 102, a secondary absorbent member 104, and a withdrawal cord 106. As shown in FIG. 1, the primary absorbent member 102 of the tampon 100 includes an insertion end 110 and a withdrawal end 108. To provide a frame of reference for the present discussion, the tampon 100 is shown in FIG. 2 with a longitudinal axis 112 and a lateral axis 114. With further reference to FIGS. 2 and 3, the periphery of the primary absorbent member 102 may be defined by a first end edge 116 and an opposing second end edge 118 separated by and connected with a first longitudinal side edge 120 and a second longitudinal side edge 122. The primary absorbent member 102 may also comprise a first surface 124 and an opposing second surface 126 extending between the first end edge 116 and the second end edge 118 and extending between the first longitudinal side edge 120 and the second longitudinal side edge 122.

As shown in FIG. 2, prior to compression, the primary absorbent member 102 may be formed in various shapes and sizes and may be formed with various materials and structures. For example, as shown in FIG. 2, the primary absorbent member may include a batt of absorbent material with a chevron shape. It is to be appreciated that the primary absorbent member 102 may be formed in other shapes, such as rectangular, trapezoidal, triangular, and hemispherical shapes. The primary absorbent member 102 may also be formed as a unitary member structure or a laminate structure which includes discrete layers. For example, as shown in FIG. 2, the primary absorbent member may comprise outer layers 128 and at least one intermediate layer 130 positioned between the outer layers 128. The primary absorbent member may include various additional structures and materials such as described for example in U.S. Pat. No. 6,258,075 and U.S. Patent Publication No. 2004/0019317A1, both of which are incorporated by reference herein. It is to be appreciated that the discrete layers may include different materials (or same materials if desired). For example, one layer may include primarily rayon, while another layer (or layers) may include primarily cotton. In some configurations, the outer layer 128 may be a batt formed by a rayon material which is available from Acordis Fibers Ltd. as Galaxy rayon, while the intermediate layer 130 may be a batt formed by a cotton material which is available from Acordis Fibers Ltd.

It is to be appreciated that the primary absorbent member 102 may be constructed from a wide variety of liquid-absorbing materials used in absorbent articles, such as rayon, cotton, and comminuted wood pulp, which may be generally referred to as airfelt. Examples of additional absorbent materials include creped cellulose wadding; melt-blown polymers including coform; chemically stiffened, modified or cross-linked cellulosic fibers; synthetic fibers such as crimped polyester fibers; peat moss; foam; tissue including tissue wraps and tissue laminates; or any equivalent material or combinations of materials, or mixtures thereof. Absorbent materials may also comprise cotton, rayon (including tri-lobal and conventional rayon fibers, and needle punched rayon), folded tissues, and woven or nonwoven materials of synthetic and/or natural fibers. The primary absorbent member 102 may include a single material or combinations of such materials. For example, primary absorbent member 102 may include a uniform material of a unitary material of rayon or cotton, or a blended material of rayon and cotton. Additionally, superabsorbent materials, such as superabsorbent polymers or absorbent gelling materials may be incorporated into the primary absorbent member 102. In some configurations, the absorbent material of the primary absorbent member 102 may be surrounded with a liquid permeable overlap material. Such overlap materials may comprise rayon, cotton, bicomponent fibers, or other natural or synthetic fibers known in the art.

The primary absorbent member 102 may be formed of a soft absorbent material such as rayon, cotton (including either long fiber cotton or cotton linters) or other suitable natural or synthetic fibers or sheeting. The materials for primary absorbent member 102 may be either a fabric, web, or batt that is formed by any suitable process known in the art such as airlaying, carding, wetlaying, hydroentangling, and other known techniques. Rayon material may be any suitable material used in disposable absorbent articles known in the art. Cotton material may also be used in the primary absorbent member 102. Such cotton material may include, long fiber cotton, short fiber cotton, cotton linters, T-fiber cotton, card strips, and comber cotton. Cotton materials may also be a scoured and bleached cotton absorbent with a glycerin finish, a leomin finish, or other suitable finish.

It is also to be appreciated that the primary absorbent member 102 may include various sizes and thicknesses suitable for compression into a tampon having a size which facilitates insertion. In some configurations, the primary absorbent member may be about 9 cm in longitudinal length and about 4.5 cm in lateral width. Additionally, the lengths and widths of the primary absorbent member 102 may be configured in various ranges to facilitate width-wise expansion of the tampon in use. It is also to be appreciated that the primary absorbent member 102 may be configured with various oval basis weights. For example, in some configurations, the overall basis weight of the primary absorbent member 102 may be from about 150 g/m2 to about 750 g/m2.

With continued reference to FIGS. 2 and 3, the periphery of the secondary absorbent member 104 may be defined by a first end edge 132 and an opposing second end edge 134 separated by and connected with a first longitudinal side edge 136 and a second longitudinal side edge 138. The secondary absorbent member 104 may also comprise a first surface 140 and an opposing second surface 142 extending between the first end edge 132 and the second end edge 134 and extending between the first longitudinal side edge 136 and the second longitudinal side edge 138. As shown in FIGS. 2 and 3, the second surface 142 of the secondary absorbent member 104 is positioned in contact with and in a facing relationship with the first surface 124 of the primary absorbent member 102. The secondary absorbent member 104 may be positioned in various locations on the primary absorbent member 102. For example, the secondary absorbent member 104 may be positioned in a generally laterally central position between the first longitudinal side edge 120 and the second longitudinal side edge 122 of the primary absorbent member 102. For example, the secondary absorbent member 104 may be positioned such that the first end edge is located in a generally longitudinally central position between the first end edge 116 and the second end edge 118 of the primary absorbent member 102. In addition, the secondary absorbent member 104 may be positioned proximate the withdrawal end 108 of the primary absorbent member 102. For example, the secondary absorbent member 104 may extend longitudinally along the primary absorbent member 102 such that a portion of the secondary absorbent member 104 and second edge 134 thereof are positioned outboard of the second end edge 118 of the primary absorbent member 102.

It is to be appreciated that the secondary absorbent member 104 may be formed in various shapes and sizes and may be formed with various materials and structures. In some configurations, the secondary absorbent member 104 may be arranged in a wide variety of shapes and configurations and may be generally cylindrical, spherical, semi-spherical, disc-like, planar, rectangular, "skirt-like" in shape, or may comprise "tufts" or whips of absorbent elements. The size of the secondary absorbent member 104 may vary according to its shape. For example, the secondary absorbent member 104 may be generally cylindrical and elongated. The secondary absorbent member 104 may also be configured with a longitudinal length that is the same as, less than, or greater than the longitudinal length of the primary absorbent member 102.

The secondary absorbent member 104 may be constructed from any of the materials described above for suitable as use in the primary absorbent member 102, such as rayon and cotton for example. In some configurations, the same materials are used in the construction of the secondary absorbent member 104 as are used in the primary absorbent member 102. The secondary absorbent member 104 may also include a suitable nonwoven structure, such as described above. In some configurations, the secondary absorbent member 104 is hydrophilic. In some embodiments, the secondary absorbent material 104 may have an advancing contact angle greater than the advancing contact angle of the primary absorbent member 102 and/or the withdrawal cord 106 (or other withdrawal mechanism), such that fluid is preferentially directed toward and absorbed by the primary absorbent member 102. In some configurations, the secondary absorbent member 104 may be treated to make it less absorbent than the primary absorbent member 102. The secondary absorbent member 104 may include various materials such, as described for example in U.S. Pat. No. 6,258,075 and U.S. Patent Publication No. 2004/0019317A1, both of which are incorporated by reference herein.

For a more detailed description of hydrophilicity and contact angles see the following publications which are incorporated by reference herein: The American Chemical Society Publication entitled "Contact Angle, Wettability, and Adhesion," edited by Robert F. Gould, and copyrighted in 1964; and TRI/Princeton Publications, Publication Number 459, entitled "A Microtechnique for Determining Surface Tension," published in April 1992, and Publication Number 468 entitled, "Determining Contact Angles Within Porous Networks," published in January 1993, both edited by Dr. H. G. Heilweil.

In some configurations, the secondary absorbent member 104 may optionally be provided with a mechanism to preferentially direct acquired fluid toward the primary absorbent member 102. Examples of such a driving force are the use of a hydrophilicity gradient. Other mechanisms may include a density or capilarity gradient, or an osmotic driving force. The secondary absorbent member 104 may be provided with loose fiber ends to add a textured surface to the material. Capillary channel fibers may optionally be incorporated into the secondary absorbent material 104 in order to provide the driving force for acquired fluid.

Referring again to FIGS. 2 and 3, the withdrawal cord 106 is positioned in contact with and in a facing relationship with the first surface 140 of the secondary absorbent member 104. Depending on the longitudinal lengths of and relative positioning of the secondary absorbent member 104 and the primary absorbent member 102, the withdrawal cord 106 may also be positioned in contact with and in a facing relationship with the first surface 124 of the primary absorbent member 102. The withdrawal cord 106 may extend along a length from a first end 144 to a second end 146. The withdrawal cord 106 may be positioned in various locations on the primary absorbent member 102 and/or the secondary absorbent member 104. For example, the withdrawal cord 106 may be positioned in a generally laterally central position between the first longitudinal side edge 120 and the second longitudinal side edge 122 of the primary absorbent member 102. The withdrawal cord 106 may also be positioned in a generally laterally central position between the first longitudinal side edge 136 and the second longitudinal side edge 138 of the secondary absorbent member 104. The withdrawal cord 106 may also be positioned relative to the primary absorbent member 102 and the secondary absorbent member 104 so as to define a length having a proximal end portion 148, a distal end portion 150, and central portion 152 between the proximal end portion 148 and the distal end portion 150.

The proximal end portion 148 and the central portion 152 and may be connected with the primary absorbent member 102 and/or the secondary absorbent member 104. The distal end portion 150 of the withdrawal cord 106 may not be connected with the primary absorbent member 102 and the secondary absorbent member 104 and may be used to withdraw the tampon 100 after use. For example, the first end 144 of the withdrawal cord 106 may be positioned adjacent to or coterminous with the first end edge 116 of the primary absorbent member 102. From the first end 144, the proximal end portion 148 of the withdrawal cord 106 may extend longitudinally along the first surface 124 of the primary absorbent member 102 toward the second end edge 118 of the primary absorbent member 102. The proximal end portion 148 and the central portion 152 of the withdrawal cord 106 may also extend longitudinally along the first surface 140 of the secondary absorbent member 104 from the first end edge 132 to the second end edge 134. From the second end edge 134 of the secondary absorbent member 104, the distal end portion 150 of the withdrawal cord 106 may extend from the second end edge 134 of the secondary absorbent member 104 to the second end 146 such that the distal end portion 150 of the withdrawal cord 106 is positioned outboard the second end edge 118 of the primary absorbent member 102 and the second end edge 134 of the secondary absorbent member 104.

As shown in FIGS. 1 and 2, the withdrawal cord 106, the secondary absorbent member 104, and the primary absorbent member 102 may be stitched together with at least one thread 154. The thread 154 may be sewn through and along the entire length of the withdrawal cord 106. For example, as shown in FIG. 2, the thread 154 may extend through both the withdrawal cord 106 and the primary absorbent member 102 along the proximal end portion 148 of the withdrawal cord 106. In addition, the one or more threads 154 may extend through the withdrawal cord 106, the secondary absorbent member 104, and the primary absorbent member 102 along the proximal end portion 148 and central portion 152 of the withdrawal cord 106. Further the thread 154 may extend through the withdrawal cord 106 along the distal end portion 150 to the second end 146. Various manners of stitching known in the art can be used. In some configurations, the withdrawal cord 106 may be stitched with the thread 154 according to the stitching manner called "Double Ring Stitching" which is described in the Japanese Industrial Standards (JIS) No. B 9070.

It is to be appreciated that the withdrawal cord 106 may be configured in various ways and from different types of materials with various properties. For example, the withdrawal cord 106 may be formed from one or more continuous strings that are twisted or braided. The withdrawal cord may be configured as a ribbon, loop, tab, or the like. In some configurations, the withdrawal cord 106 may not have uniform properties throughout its length. For example, the proximal end portion 148 and central portion 152 of the withdrawal cord 106 may be absorbent while the distal end portion 150 may be non-absorbent. Other properties such as wicking ability, hydrophilicity, density, capillary size, width, thickness, and the like can also vary along the length of the withdrawal cord 106. In some configurations, the density of material which comprises the withdrawal cord 106 may be lower than the density of the primary absorbent member 102. In some configurations, the secondary absorbent member 104 may be more hydrophilic than the withdrawal cord 106. The withdrawal cord 106, may be made substantially hydrophobic. If the entire withdrawal cord 106 is not less hydrophilic than the secondary absorbent member 104, then at least portions of the withdrawal cord 106 (such as along the location of attachment with the secondary absorbent member 104) may be less hydrophilic than the secondary absorbent member 104.

The withdrawal cord 106 may be configured to be absorbent at locations along the central portion 152 and proximal end portion 148, whereas the withdrawal cord 106 may be configured to be non-absorbent along the distal end portion. Herein, the term "non-absorbent" refers to a structure that does not retain a significant portion of deposited fluid in its structure. In some configurations, the entire length of the withdrawal cord 106 may configured to non-absorbent. In some configurations, the materials comprising the withdrawal cord 106 may be inherently non-wettable or hydrophobic or may be treated to provide such properties. For example, a coating of wax may be applied to the withdrawal cord 106 to decrease or eliminate absorbency. The withdrawal cord 106 does not necessarily need to be non-wicking, even if a non-absorbent withdrawal cord is desired. For example, it can be desirable to provide a withdrawal cord 106 in which at least the distal end portion 150 of the withdrawal cord 106 has a tendency to wick deposited fluid upwardly toward the primary absorbent member 102 and into the structure thereof.

The withdrawal cord 106 may be provided with a wicking mechanism to preferentially direct or wick acquired fluid toward the primary absorbent member 102. One example of such a driving force is produced by a hydrophilicity gradient. Other examples of the wicking mechanisms include a density gradient, a capillary gradient, and an osmotic driving force. Capillary channel fibers can optionally be incorporated into the withdrawal cord 106 in order to provide the driving force for acquired fluid described herein. An example wicking mechanism which preferentially directs acquired fluid toward the body of the primary absorbent member 102 is disclosed in the PCT Patent Publication No. WO 00/61052.

Figure 4:
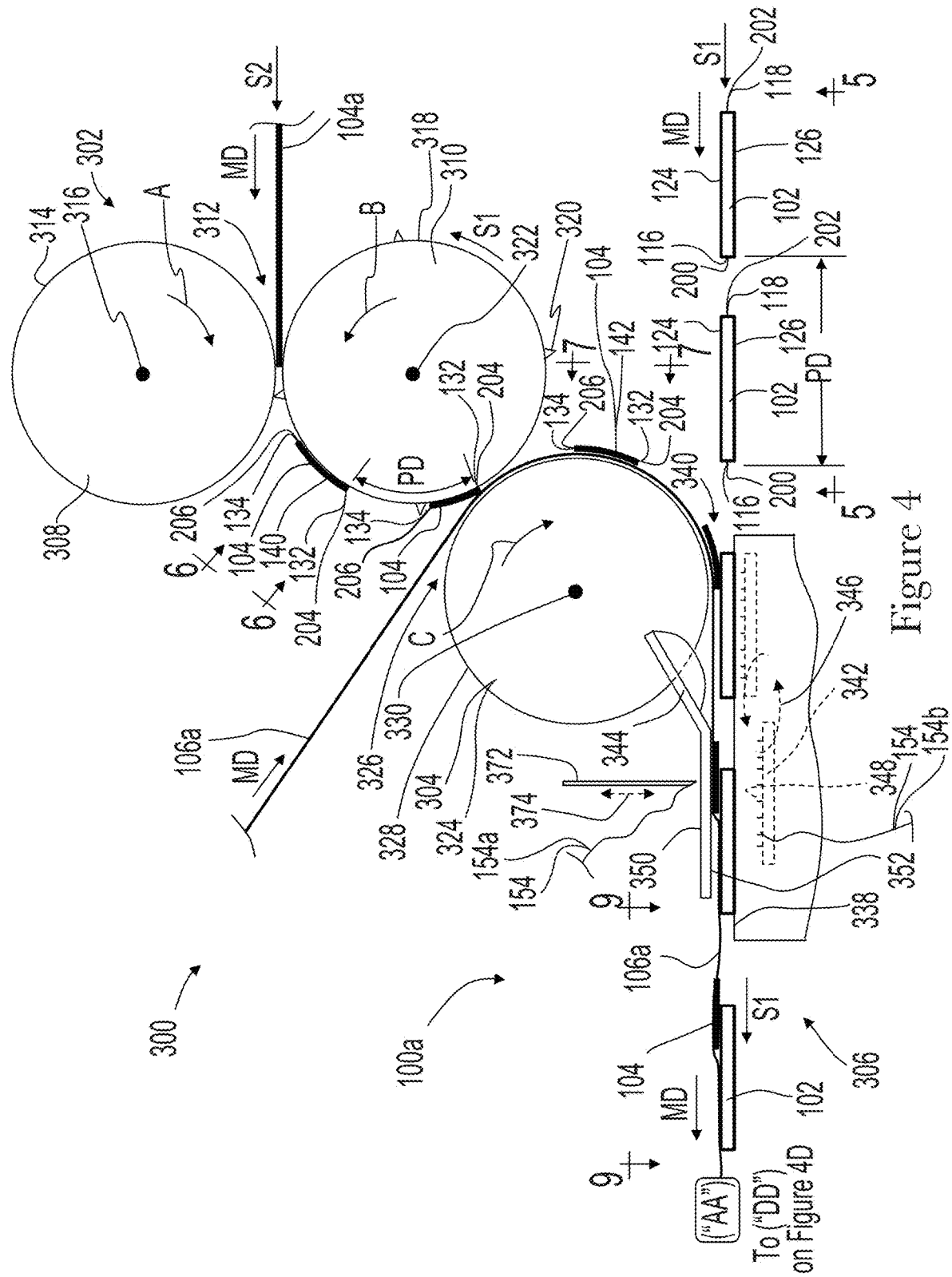
FIG. 4 is a schematic side view of a converting apparatus adapted to manufacture tampons.

As previously mentioned, the apparatuses and methods according to the present disclosure may be utilized to assemble various configurations of tampons 100. For example, FIG. 4 shows a schematic view of a converting apparatus 300 adapted to manufacture tampons 100. The method of operation of the converting apparatus 300 may be described with reference to the various components and features of the tampons 100 described above and shown in FIGS. 1-3. As discussed in more detail below with reference to FIG. 4 and others, the converting apparatus 300 may include a cutting device 302, a transfer member 304, and a sewing apparatus 306 that operate to combine primary absorbent members 102, secondary absorbent members 104, and withdrawal cords 106 into assembled tampons 100.

As shown in FIGS. 4 and 5, primary absorbent members 102 are advanced in a machine direction MD to a sewing apparatus 306 at a first speed S1. The first surface 124 and the opposing second surface 126 of each primary absorbent member 102 extend in the machine direction MD between a leading edge 200 and a trailing edge 202. The apparatus 300 may be configured to advance the primary absorbent members 102 such that the leading edge 200 may correspond with the first end edge 116 of the primary absorbent member 102, and the trailing edge 202 may correspond with the second end edge 118. The leading edges 200 of advancing the primary absorbent members 102 are separated from each other in the machine direction MD by a pitch distance, PD. It is to be appreciated that the apparatus 300 may include various types of carriers to advance the primary absorbent members 102 to the sewing apparatus 306, such as for example, conveyor belts and/or rotating drums.

Referring now to FIGS. 4 and 6, a continuous length of secondary absorbent members 104a advances in the machine direction MD to the cutting device 302 at a second speed S2. The cutting device 302 cuts discrete secondary absorbent members 104 from the continuous length of secondary absorbent members 104a. As shown in FIG. 4, the cutting device 302 may include an anvil roll 308 positioned adjacent a knife roll 310 to define a nip 312 therebetween. The anvil roll 308 may include an outer circumferential surface 314 adapted to rotate about an axis 316 in a direction A. And the knife roll 310 may include an outer circumferential surface 318 and one or more blades 320. The knife roll may also be adapted to rotate about an axis 322 in a direction B opposite direction A such that the outer circumferential surface 318 advances at the first speed S1, wherein the first speed S1 is greater than the second speed S2.

With continued reference to FIGS. 4 and 6, as the continuous length of secondary absorbent members 104a advances through the nip 312 between the anvil roll 308 and the knife roll 310, the blade 320 operates to cut discrete a secondary absorbent member 104 from the continuous length of secondary absorbent members 104a. Because the outer circumferential surface 318 of the knife roll 310 advances at the first speed S1, the cut discrete secondary absorbent member 104 may then accelerate from the second speed S2 to the first speed S1 on the outer circumferential surface 318 of the knife roll 310. As shown in FIGS. 4 and 6, the first surface 140 and the opposing second surface 142 of each secondary absorbent member 104 extend in the machine direction MD between a leading edge 204 and a trailing edge 206. The apparatus 300 may be configured to advance the secondary absorbent members 104 such that the leading edge 204 may correspond with the first end edge 132 of the secondary absorbent member 104, and the trailing edge 206 may correspond with the second end edge 134 of the secondary absorbent member 104. By accelerating the secondary absorbent members 104 from the second speed S2 to the first speed S1 on the outer circumferential surface 318 of the knife roll 310, the knife roll 310 may also be configured to cut discrete secondary absorbent members 104 from the continuous length of secondary absorbent members 104a such that consecutively cut the leading edges 204 of consecutively cut secondary absorbent members 104 are separated from each other in the machine direction MD by the pitch distance, PD. The knife roll may be configured to apply vacuum pressure to the discrete secondary absorbent members 104 to help hold the discrete secondary absorbent members 104 on the outer circumferential surface 318 as the knife roll 310 rotates.

It is to be appreciated that the cutting device 302 may be configured in various ways. In some configurations, the anvil roll 308 and/or the knife roll 310 may be heated. In some configurations, the blade 320 may be configured such that resulting cut lines and corresponding leading edges 204 and trailing edges 206 of the secondary absorbent members 104 may be straight and/or curved. As shown in FIG. 6, the leading edge 204 of the secondary absorbent member 104 may be curved so as to define a concave shape that protrudes inward in a direction toward the trailing edge 206. In addition, the trailing edge 206 of the secondary absorbent member 104 may be correspondingly curved so as to define a convex shape that protrudes outward in a direction away from the leading edge 204. The cutting device 302 may also be adapted to cut the secondary absorbent members 104 such that material along the cut line adjacent trailing edges 206 and leading edges 204 is fused and/or pressure bonded together. For example, fibrous materials from which the secondary absorbent member 104 may be constructed may be fused and/or bonded together, wherein such fusing and/or bonding may help reduce the appearance of loose fibrous ends and/or fraying of the secondary absorbent member 104 along the trailing edge 206 and/or leading edge 204. It is also to be appreciated that the positions of the knife roll 310 and anvil roll 308 may be opposite to that which is illustrated in FIG. 4, and as such, the discrete secondary absorbent members 104 may remain on the outer circumferential surface 314 of the anvil roll 308 as opposed to the knife roll 310. It is also to be appreciated that the cutting device 302 may be configured to convey and/or cut the secondary absorbent members 104 different ways. For example, the cutting device 302 may be adapted to advance the continuous length of secondary absorbent members 104a and/or the discrete secondary absorbent members 104 on a conveyor belt. In another example, the cutting device 302 may include a laser adapted to cut the discrete secondary absorbent members 104 from the continuous length of secondary absorbent members 104a.

With continued reference to FIGS. 4 and 7, during the assembly process, a continuous length of the withdrawal cord 106a may advance in the machine direction MD onto the transfer member 304. It is to be appreciated the transfer member 304 may be configured in various ways. For example, the transfer member 304 may be configured as a transfer wheel 324. As shown in FIG. 4, the transfer wheel 324 may be positioned adjacent the knife roll 310 to define a nip 326 therebetween. The transfer wheel 324 may include an outer circumferential surface 328 adapted to rotate about an axis 330 in a direction C such that the outer circumferential surface 328 advances at the first speed S1, and wherein direction C may be opposite of direction B. Secondary absorbent members 104 may be transferred from the knife roll 310 to the transfer wheel 324 at the nip 326. In particular, the secondary absorbent members 104 are transferred from the knife roll 310 to the transfer wheel 324 such that the first surfaces 140 of the secondary absorbent members 104 are positioned in a facing relationship and in contact with the outer circumferential surface 328 of the transfer wheel 324 and the continuous length of withdrawal cord 106a. The transfer wheel 324 may be configured to apply vacuum pressure to the discrete secondary absorbent members 104 to help hold the discrete secondary absorbent members 104 on the outer circumferential surface 328 as the transfer wheel 324 rotates. In addition, the knife roll 310 may be configured to apply positive air pressure, sometimes referred to as blow-off air, to the secondary absorbent members 104 adjacent the nip 326 to help remove the secondary absorbent members 104 from the knife roll 310 during transfer to the transfer wheel 324.

As shown in FIGS. 7 and 8, the outer circumferential surface 328 of the transfer wheel 324 may include a groove 332 to help guide and position the advancing continuous withdrawal cord 106a in the cross direction CD. The outer circumferential surface 328 of the transfer wheel 324 may also include apertures 334 in fluid communication with a vacuum system to apply vacuum pressure to the secondary absorbent members 104. Because the continuous withdrawal cord 106a is positioned between the outer circumferential surface 328 of the transfer wheel 324 and the secondary absorbent members 104, the apertures 334 in the transfer wheel 324 may be configured to extend in the cross direction CD to define a width that is greater than width of the continuous withdrawal cord 106a. As such, the continuous withdrawal cord 106a does not completely cover and/or block the apertures 334 in the transfer wheel 324 so as to help ensure that vacuum pressure is applied to the secondary absorbent members 104, as schematically represented by the dashed arrows 336 in FIG. 8. As discussed in more detail below, the secondary absorbent members 104 and continuous length of withdrawal cord 106a are transferred from the transfer wheel 324 and are combined with the advancing primary absorbent members 102 at the sewing apparatus 306.

As shown in FIG. 4, the sewing apparatus 306 may include a sewing support surface 338 positioned adjacent the transfer wheel 324 to define a nip 340 there between. The primary absorbent members 102 advance onto the sewing support surface 338 such that the second surface 126 of the primary absorbent members 102 are in a facing relationship and in contact with the sewing support surface 338. As the primary absorbent members 102 advance through the nip 340, the continuous withdrawal cord 106a is positioned on the first surface 124 of the primary absorbent members 102. In addition, the second surfaces 142 of the secondary absorbent members 104 are positioned in a facing relationship and in contact with the first surfaces 124 of the primary absorbent members 102. The position of the continuous withdrawal cord 106a on the first surfaces 140 of the secondary absorbent members 104 is also maintained as the secondary absorbent members 104 advance onto the primary absorbent members 102.

As shown in FIG. 4, the sewing apparatus 306 may also include a feed dog 342 and a presser foot 344. The feed dog 342 may be adapted to move in a reciprocating motion as represented by the dashed arrows 346 in FIG. 4. The feed dog 342 may also include teeth 348 that engage the second surfaces 126 of the primary absorbent members 102. In turn, the feed dog 342 pulls on the primary absorbent members 102 to help advance primary absorbent members 102, secondary absorbent members 104, and the continuous withdrawal cord 106a in the machine direction MD between the sewing support surface 338 and the presser foot 344.

It is to be appreciated that the presser foot 344 may be configured in various ways. For example, FIGS. 4A-4C show detailed views of an example presser foot 344 that may be used with the apparatuses and methods herein. As shown in FIG. 4A, the presser foot 344 may include a top surface 350 and an opposing bottom surface 352 that extend from a first end portion 354 to an opposing second end portion 356. The first end portion 354 may also be angular offset from the second end portion 356. In use, the presser foot 344 may be oriented such that the first end portion 354 is an upstream end portion 358 and the second end portion 356 is a downstream end portion 360. As such, the continuous withdrawal cord 106a, secondary absorbent members 104, and primary absorbent members 102 advance in the machine direction MD between the bottom surface 352 of the presser foot 344 and the sewing support surface 338 from the upstream end portion 358 to the downstream end portion 360. The upstream end portion 358 includes a first projection 362 and a second projection 364 separated in the cross direction CD by a notch 366. In addition, the presser foot 344 may include a first guide wall 368 and second guide wall 370 on opposing sides of the notch 366, wherein the first guide wall 368 extends downward from the first projection 362, and the second guide wall 370 extends downward from the second projection 364. As shown in FIGS. 4 and 4B, a portion of the transfer wheel 324 may be positioned in the notch 366 as well as between the first and second guide walls 368, 370. It is to be appreciated that the transfer wheel 324 may define a width in the cross direction CD that is smaller than a width of the notch 366. In some configurations, the transfer wheel 324 may define a cross directional width that is about 1 mm smaller than a cross directional width of the notch 366. In some embodiments, the presser foot 344 may also include a roller positioned in the notch 366 to help ensure that the continuous withdrawal cord 106a, secondary absorbent members 104, and primary absorbent members 102 advance relatively smoothly between the bottom surface 352 of the presser foot 344 and the sewing support surface 338.

With continued reference to FIG. 4, the sewing apparatus 306 includes a needle 372 adapted to sew a thread 154 through the continuous length of withdrawal cord 106a, the secondary absorbent member 104, and the primary absorbent member 102 advancing between the pressure foot 344 and the sewing support surface 338. As shown in FIG. 4, the needle 372 may be adapted to move in a reciprocating motion indicated by the dashed arrow 374. An aperture 376, such as shown in FIG. 4B, in the presser foot 344 provides an opening through which the needle and thread can travel. In turn, the needle 372 may be loaded with a first thread 154a adapted to enter and withdraw from the advancing continuous withdrawal cord 106a as well as the primary absorbent members 102 and secondary absorbent members 104. As such, stitching may be formed by the up-and-down (or in-and-out) motion of the needle 372 engaging the first thread 154a with a second thread 154b, also referred to as a looper thread, introduced below the continuous withdrawal cord 106a and the primary absorbent members 102 and secondary absorbent members 104 from underneath the sewing support surface 338. The sewing operation may be continuous such that the threads 154a, 154b form stitches along the entire length of the continuous withdrawal cord 106a, the primary absorbent member 102, and the secondary absorbent member 104 to create a continuous length of tampons 100a. As shown in FIGS. 4 and 9, the continuous length of tampons 100a advance in the machine direction MD from between the presser foot 344 and the sewing support surface 338. It is to be appreciated that the apparatus 300 may include various types of carriers to advance the continuous length of tampons 100a from the sewing apparatus 306, such as for example, conveyor belts and/or rotating drums.

Figure 4D:
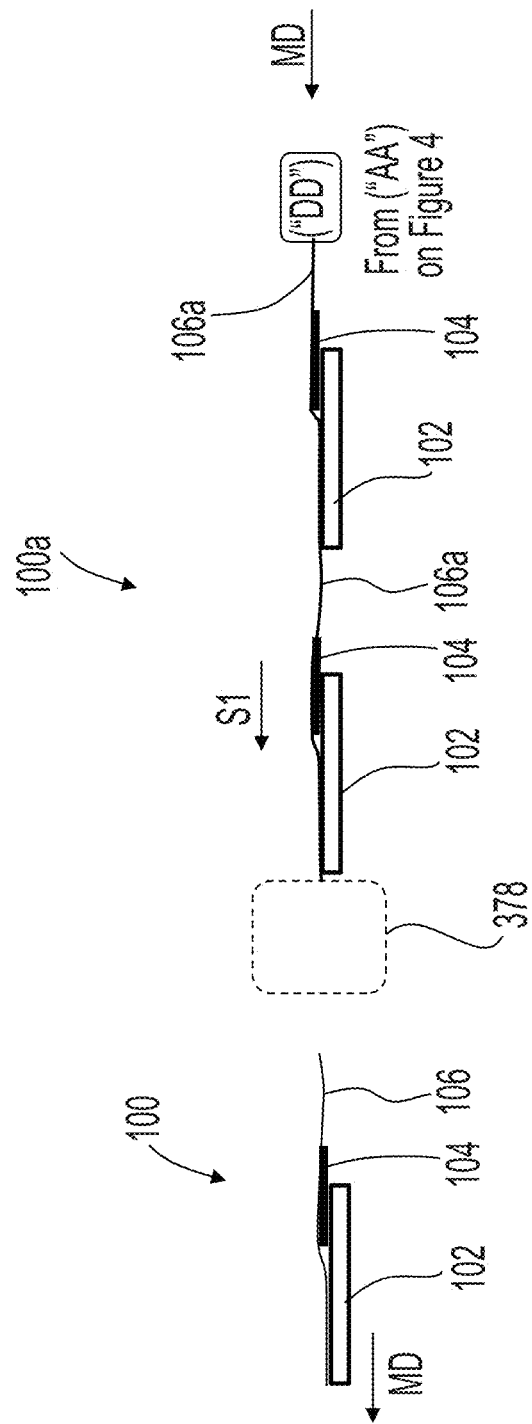
FIG. 4D is a schematic side view of a discrete tampon cut from a continuous length of tampons from FIG. 4.

As shown in FIG. 4D, the continuous length of tampons 100a may advance to a cord cutter apparatus 378 that cuts the continuous withdrawal cord 106a to separate the continuous length of tampons 100a into discrete tampons 100, such as shown for example in FIGS. 1 and 2. The cord cutter apparatus 378 is generically represented by dashed rectangle in FIG. 4D. It is to be appreciated the cord cutter apparatus 378 may be configured in various ways, such as for example, a knife roll and anvil roll. As discussed above with reference to FIGS. 1 and 2, both the withdrawal cord 106 and the primary absorbent member 102 may be stitched together along the proximal end portion 148 of the withdrawal cord 106. In addition, the withdrawal cord 106, the secondary absorbent member 104, and the primary absorbent member 102 may be stitched together along the proximal end portion 148 and central portion 152 of the withdrawal cord 106. Further, the withdrawal cord 106 may be stitched along the distal end portion 150 to the second end 146.

It is to be appreciated that the assembly processes herein may be configured in various ways to assemble tampons 100 with various component configurations. For example, the primary absorbent member 102 may be surrounded with a liquid permeable overwrap material. Such overwrap materials may comprise rayon, cotton, bicomponent fibers, or other suitable natural or synthetic fibers known in the art. As such, the assembly process may be configured to apply the overwrap material to the primary absorbent member 102 before being combined with the secondary absorbent member 104. In some configurations, the assembly process may be configured to apply the overwrap material to the primary absorbent member 102 and possibly the secondary absorbent member 104 after the primary absorbent member 102 and the secondary absorbent member 104 are combined.

Figure 10:
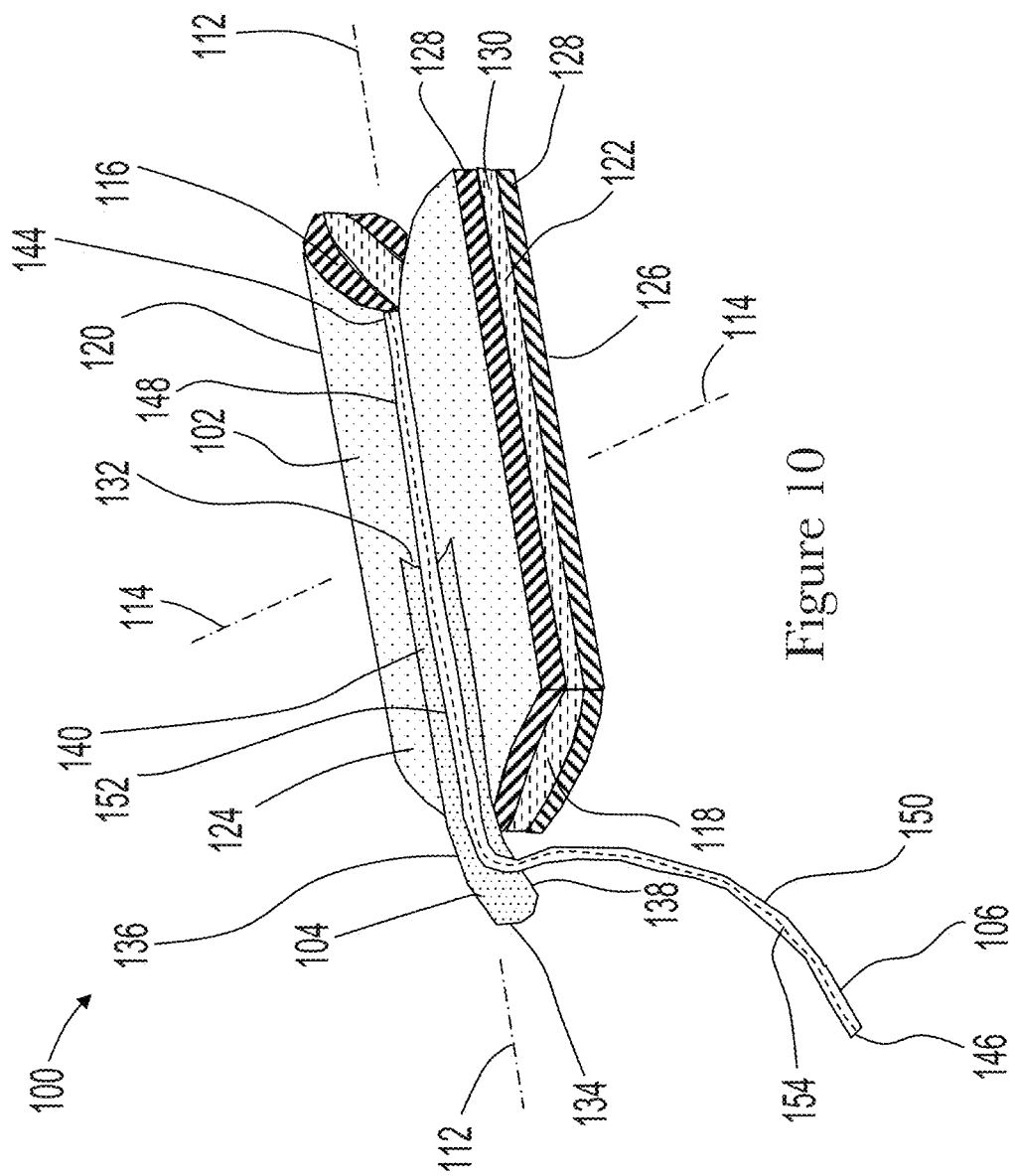
FIG. 10 is a perspective view of another embodiment of a tampon blank prior to compression into a tampon.

In another example, the assembly process may be configured to assemble tampons 100 where the withdrawal cord is not sewn along the entire length of the secondary absorbent member 104. For example, as shown in FIG. 10, the first end 144 of the withdrawal cord 106 may be positioned adjacent to or coterminous with the first end edge 116 of the primary absorbent member 102. From the first end 144, the proximal end portion 148 of the withdrawal cord 106 may extend longitudinally along the first surface 124 of the primary absorbent member 102 toward the second end edge 118 of the primary absorbent member 102. The proximal end portion 148 and the central portion 152 of the withdrawal cord 106 may also extend longitudinally along the first surface 140 of the secondary absorbent member 104 from the first end edge 132 toward the second end edge 134, and the withdrawal cord 106 may extend outboard of the secondary absorbent member 104 from the second longitudinal side edge 138 (or the first longitudinal side edge 136). From the second longitudinal side edge 138 (or the first longitudinal side edge 136) of the secondary absorbent member 104, the distal end portion 150 of the withdrawal cord 106 may extend from the second longitudinal side edge 138 (or first longitudinal side edge 136) of the secondary absorbent member 104 to the second end 146 such that the distal end portion 150 of the withdrawal cord 106 is positioned outboard the second end edge 118 of the primary absorbent member 102 and the second longitudinal side edge 138 (or first longitudinal side edge 136) of the secondary absorbent member 104.

Figure 11:
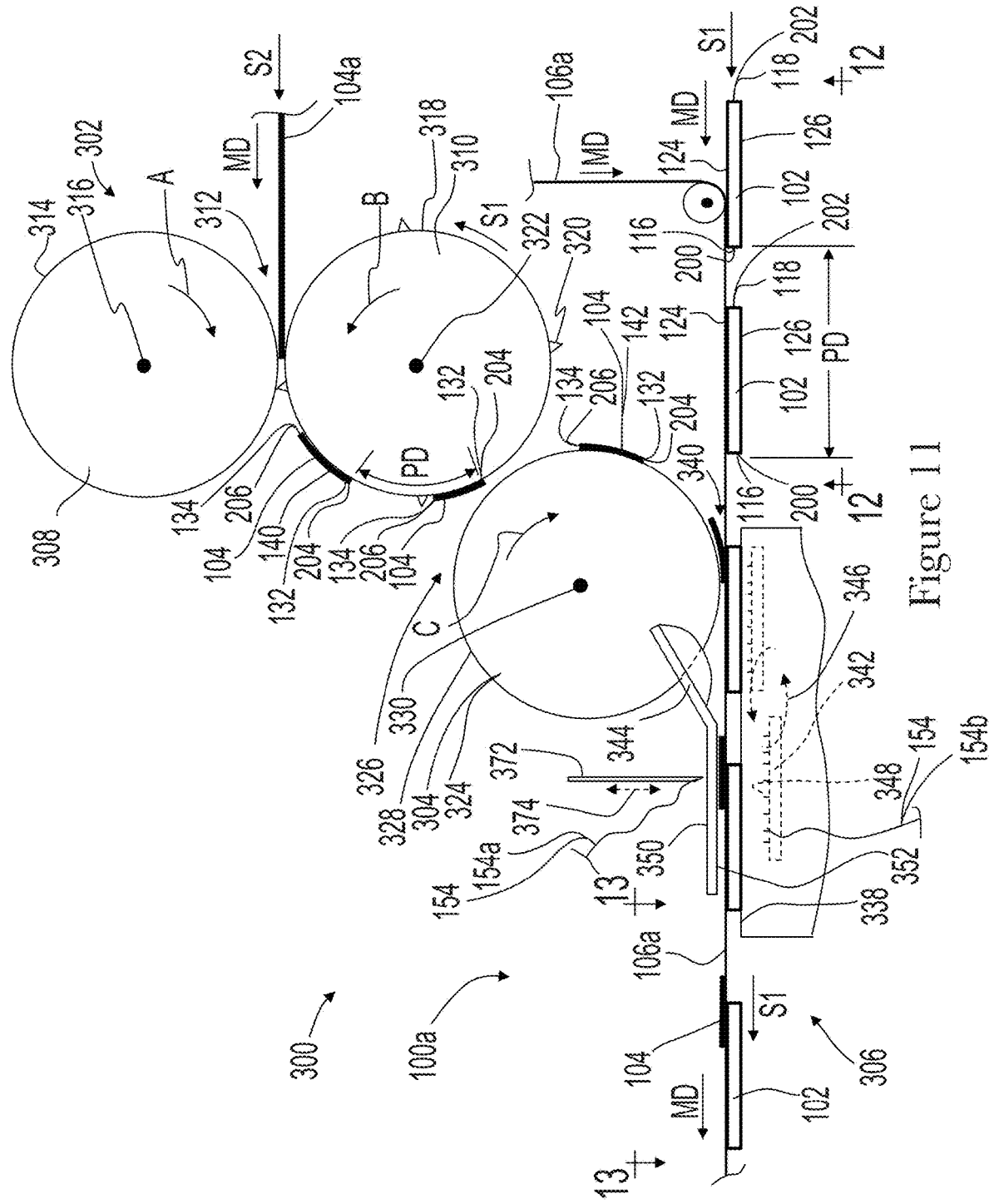
FIG. 11 is a schematic side view of another embodiment of a converting apparatus adapted to manufacture tampons.

In another example, the assembly processes herein may be configured to position the withdrawal cord 106 between the first surface 124 of the primary absorbent member 102 and the second surface 142 of the secondary absorbent member 104. For example, FIG. 11 shows an apparatus 300 similar to the apparatus shown in FIG. 4, except the continuous length of withdrawal cord 106a in FIG. 11 may be advanced and positioned on the first surface 124 of the advancing primary absorbent members 102 before the primary absorbent members 102 advance through the nip 340. As shown in FIGS. 11-13, as the primary absorbent members 102 advance through the nip 340, the continuous withdrawal cord 106a is positioned on the first surface 124 of the primary absorbent members 102. In addition, the second surfaces 142 of the secondary absorbent members 104 are positioned in a facing relationship and in contact with the first surfaces 124 of the primary absorbent members 102 such that the continuous withdrawal cord 106a is sandwiched between the first surface 124 of the primary absorbent member 102 and the second surface 142 of the secondary absorbent member 104.

It is also to be appreciated that the assembly processes herein may be configured to form an assemblage of a continuous length of withdrawal cord 106a and secondary absorbent members 104, wherein the assemblage is subsequently combined with discrete primary absorbent members 102. For example, discrete secondary absorbent members 104 may be connected with a continuous length of withdrawal cord 106*a* such that the leading edges of consecutively spaced secondary absorbent members 104 are separated from each other in the machine direction MD by the pitch distance, PD, as discussed above. The secondary absorbent members 104 may be connected with the continuous length of withdrawal cord 106*a* in various ways to create the assemblage. For example, the secondary absorbent members 104 may be folded or wrapped around the withdrawal cord 106*a* such that the secondary absorbent member 104 fully envelope discrete lengths of the withdrawal cord 106*a*.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making a tampon, the method comprising steps of:
   advancing primary absorbent members in a machine direction, wherein each primary absorbent member comprises a first surface and an opposing second surface extending in the machine direction between a leading edge and a trailing edge, wherein the leading edges of advancing the primary absorbent members are separated from each other in the machine direction by a pitch distance;
   advancing discrete secondary absorbent members, wherein each discrete secondary absorbent member extends in the machine direction between a leading edge and a trailing edge;
   separating the leading edges of the advancing discrete secondary absorbent members from each other in the machine direction by the pitch distance;
   advancing a continuous cord in the machine direction;
   advancing the continuous cord and the discrete secondary absorbent members on a rotating transfer wheel;
   positioning the continuous cord on a first discrete secondary absorbent member;
   positioning the first discrete secondary absorbent member in contact with a first primary absorbent member;
   combining the continuous cord, the first discrete secondary absorbent member, and the first primary absorbent member.

2. The method of claim 1, further comprising:
   advancing a continuous length of secondary absorbent members; and
   cutting the discrete secondary absorbent members from the continuous length of secondary absorbent members.

3. The method of claim 2, wherein the step of cutting further comprises advancing the continuous length of secondary absorbent members between a rotating knife roll and anvil roll.

4. The method of claim 2, wherein the discrete secondary absorbent members comprise a plurality of fibers, wherein the step of cutting discrete secondary absorbent members further comprises bonding the fibers together at the trailing edge.

5. The method of claim 1, wherein the step of separating further comprises accelerating the secondary absorbent members.

6. The method of claim 1, further comprising advancing the continuous cord, the discrete secondary absorbent members, and the primary absorbent members between a presser foot and a sewing support surface.

7. The method of claim 1, further comprising applying overwrap material to the first primary absorbent member before positioning a surface of the first discrete secondary absorbent member in contact with and in a facing relationship with the first surface of a first primary absorbent member.

8. The method of claim 1, wherein the continuous cord extends across the trailing edges of the discrete secondary absorbent members.

9. The method of claim 1, wherein the discrete secondary absorbent members comprise side edges extending between the leading edges and the trailing edges thereof, and wherein the continuous cord extends across the leading edges and the side edges of the discrete secondary absorbent members.

10. The method of claim 1, further comprising:
    advancing a continuous length of secondary absorbent members; and
    cutting the discrete secondary absorbent members from the continuous length of secondary absorbent members.

11. A method for making a tampon, the method comprising steps of:
    advancing primary absorbent members at a first speed, S1, wherein each primary absorbent member comprises a first surface and an opposing second surface extending in the machine direction between a leading edge and a trailing edge, wherein the leading edges of advancing the primary absorbent members are separated from each other in the machine direction by a pitch distance;
    advancing a continuous length of secondary absorbent members at a second speed, S2, wherein the second speed, S2, is less than the first speed, S1;
    cutting discrete secondary absorbent members from the continuous length of secondary absorbent members, wherein each discrete secondary absorbent member comprises extends in the machine direction between a leading edge and a trailing edge;
    accelerating the discrete secondary absorbent members from the second speed, S2, to the first speed, S1;
    advancing a continuous cord in the machine direction;
    advancing the continuous cord and the discrete secondary absorbent members at the first speed S1 on a rotating transfer wheel;
    positioning the continuous cord on the discrete secondary absorbent members;
    positioning a first discrete secondary absorbent member in contact with a first primary absorbent member; and combining the continuous cord, the first discrete secondary absorbent member, and the first primary absorbent member.

12. The method of claim 11, wherein the step of accelerating further comprises separating the leading edges of the advancing discrete secondary absorbent members from each other in the machine direction by the pitch distance.

13. The method of claim 11, further comprising advancing the continuous cord, the first discrete secondary absorbent member, and the first primary absorbent member between a presser foot and a sewing support surface.

14. A method for making a tampon, the method comprising steps of:
advancing primary absorbent members in a machine direction, wherein each primary absorbent member comprises a first surface and an opposing second surface extending in the machine direction between a leading edge and a trailing edge, wherein the leading edges of advancing the primary absorbent members are separated from each other in the machine direction by a pitch distance;
advancing discrete secondary absorbent members, wherein each discrete secondary absorbent member extends in the machine direction between a leading edge and a trailing edge;
separating the leading edges of the advancing discrete secondary absorbent members from each other in the machine direction by the pitch distance;
advancing a continuous cord in the machine direction;
advancing the continuous cord and the discrete secondary absorbent members on a rotating transfer wheel;
positioning the continuous cord on a first primary absorbent member;
positioning a first discrete secondary absorbent member in contact with the first primary absorbent member; and
combining the continuous cord, the first discrete secondary absorbent member, and the first primary absorbent member.

15. The method of claim 14, further comprising advancing the continuous cord, the discrete secondary absorbent members, and the primary absorbent members between a presser foot and a sewing support surface.

16. The method of claim 10, wherein the discrete secondary absorbent members comprise a plurality of fibers, wherein the step of cutting discrete secondary absorbent members further comprises bonding the fibers together at the trailing edge.

17. The method of claim 14, further comprising applying overwrap material to the first primary absorbent member before positioning a surface of the first discrete secondary absorbent member in contact with and in a facing relationship with a first surface of a first primary absorbent member.

18. The method of claim 14, wherein the continuous cord extends across the trailing edges of the discrete secondary absorbent members.

19. The method of claim 14, wherein the discrete secondary absorbent members comprise side edges extending between the leading edges and the trailing edges thereof, and wherein the continuous cord extends across the leading edges and the side edges of the discrete secondary absorbent members.

* * * * *